United States Patent
Reichert et al.

(10) Patent No.: US 6,465,227 B1
(45) Date of Patent: Oct. 15, 2002

(54) SPHERICAL PARTICLES CONTAINING MICROORGANISM CELLS HAVING ENZYME ACTIVITY

(75) Inventors: Arno Reichert, Innsbruck; Waander Riethorst, Breitenbach a. Inn; Franz Knauseder, Kirchbichl; Norbert Palma, Breitenbach a. Inn, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/508,030

(22) PCT Filed: Sep. 8, 1998

(86) PCT No.: PCT/EP98/05729

§ 371 (c)(1),
(2), (4) Date: Apr. 3, 2000

(87) PCT Pub. No.: WO99/13058

PCT Pub. Date: Mar. 18, 1999

(30) Foreign Application Priority Data

Sep. 9, 1997 (AT) ............................. 1505/97
Sep. 9, 1997 (AT) ............................. 1506/97
Sep. 9, 1997 (AT) ............................. 1507/97

(51) Int. Cl.$^7$ .................. C12N 11/08; C12N 11/04; C12N 11/00; C12N 11/02
(52) U.S. Cl. .............. 435/180; 435/182; 435/174; 435/177
(58) Field of Search .................. 435/180, 181, 435/182, 177, 174

(56) References Cited

U.S. PATENT DOCUMENTS 3,857,824 A * 12/1974 Atkins
4,892,825 A * 1/1990 Wumpelmann et al.
5,252,445 A * 10/1993 Timmerman et al.
5,424,196 A * 6/1995 Cambiaghi et al.
5,424,203 A * 6/1995 Vincenzi
5,618,687 A * 4/1997 Wong et al.

FOREIGN PATENT DOCUMENTS

| EP | 0 243 167 A | 10/1987 |
| EP | 0 436 355 A | 7/1991 |
| EP | 0 473 008 A | 3/1992 |
| EP | 0 496 993 A | 8/1992 |
| EP | 0 601 996 A | 6/1994 |
| GB | 2 275 925 A | 9/1994 |
| WO | WO-9012110 A1 * | 10/1990 |
| WO | WO-9602577 A1 * | 2/1996 |

OTHER PUBLICATIONS

Kurillova et al., Calcium pectate gel beads for cell entrapment (1992) Biotech. and Appl. Biochem., vol. 16, pp. 236–251.*

Bodalo et al., Stabilization studies of l–aminoacylase–producing pseudomonas sp. BA2 immobilized calcium alginate gel (1997) Enzyme and Microbial Technology, vol. 21, pp. 64–69.*

* cited by examiner

Primary Examiner—Jon P. Weber
(74) Attorney, Agent, or Firm—Gabriel Lopez; Lydia McNally; George R. Dohmann

(57) ABSTRACT

A process is presented for producing spherical particles containing microorganism cells having desired enzyme activity. The process comprises the steps of mixing the cells directly with a primary or secondary amine-containing polymer, combining the resulting mixture with an organic solvent to form a two-phase system, and then adding a bifunctional cross-linking agent to yield the spherical particles. The preferred enzyme activities are D-amino acid oxidase and glutarylacylase activities.

4 Claims, No Drawings

SPHERICAL PARTICLES CONTAINING MICROORGANISM CELLS HAVING ENZYME ACTIVITY

This application is a 371 of PCT/EP98/05729, filed Aug. 9, 1998, which claims priority to Austrian applications Ser. No. 1505/97, filed Sep. 9, 1997, Ser. No. 1506/97, filed Sep. 9, 1997 and Ser. No. 1507/97, filed Sep. 9, 1997.

The present invention relates to a process for inhibition of esterase activity in enzyme preparations, e.g. useful in enzymatic camlysed production of 7-aminocephalosporanic acid (7-ACA); and to the production of enzyme preparations, e.g. useful in 7-ACA and/or 7-amino-3-hydroxymethyl-3-cephem-4-carboxylic acid production.

7-ACA is a key intermediate in the production of e.g. pharmaceutically, active cephalosporin antibiotics, e.g. 7-ACA may be acylated at the amine group in position 7 of the ring system, e.g. a group known as a valuable group in the production of cephalosporin antibiotics or known as a valuable group in an intermediate for their production; e.g. to obtain a 7-arninoacylated cephalosporin having a methylaceroxy group in position 3 of the ring system, such as cefotaxime, cerpodoxime (proxetil), cephaloglycin, and in the production of other cephalosporin antibiotics or intermediates for their production which may be derived from 7-ACA; e.g. by further reacting the methylacetoxy group in position 3 of the ring system to obtain a 3-substituted cephalosporin substituted by a group which is different from the acetoxymethyl group; e.g. a group known as a valuable group in the production of cephalosporin antibiotics or known as a valuable group in an intermediate for their production; e.g. by nucleophilic substitution of the aceroxy group, or e.g. by deacerylation of the methylacetoxy group to obtain the hydroxymethyl group (e.g. HACA); and e.g. further reacting a hydroxymethyl group obtained in position 3 of the ring system, e.g. by nucleophilic substitution of the hydroxy group; or removal of the hydroxy function of a hydroxymethyl group or removal of the hydroxymethyl group in position 3 of the ring system: and, if desired, esterification of the carboxylic group in position 4 of the ring system, e.g. by a group known as a valuable group in the production of cephalosporin antibiotics or known as a valuable group in an intermediate for their production: and, if desired, salt and/or solvent formation of a cephalosporin compound obtained in such a reaction e.g. according to a conventional method. 7-ACA and HACA may e.g. be obtained from cephalosporin C (Ceph C) by deacylation of the amine group in position 7 of the ring system, and deacetylation of the methylaceroxy group in position 3 of the ring system, respectively, e.g. enzymatically. An enzyme useful in enzymatic Ceph C deacylation is e.g. D-amino acid oxidase (DAO) which catalyses the oxydative desamination of Ceph C to form giutaryl-7-aminocephalosporanic acid (G1-7-ACA) via the intermediate a-ketoadipoyl-7-aminocephalosporanic acid (KA-7-ACA). G1-7-ACA may be hydrolised to obtain glutaric acid and 7-ACA, e.g. by a glutarylacylase (GAC). It is known that DAO and GAC containing enzyme preparations, such as microorganism cells may contain esterase activity additionally. Undesired deacerylation of the side chain in position 3 of the ring structure of the cephalosporin may occur, e.g. due to the presence of esterase activity in enzymatically catalysed Ceph C deacylation, e.g. 3-hydroxymethyl derivatives of Ceph C and G1-7-ACA may be formed. This may result in a significant decrease of 7-ACA quality and yield. Conventional methods for decreasing esterase activity present in the presence of DAO activity by acetone or $CuSO_4$ treatment may decrease esterase activity incompletely.

It was now surprisingly found that the treatment of a mixture having esterase activity in the presence of DAO activity or having esterase activity in the presence of GAC activity with phenyimethyisulphonyl fluoride (PMSF) may decrease esterase activity considerably, e.g. substantially complete, whereas DAO, or GAC activity, respectively may remain high, e.g. substantially unchanged. This finding is surprising because according to the present invention PMSF, known e.g. as an irreversible inhibitor of serine containing proteins by serine sulphonviation, may decrease esterase activity present in the presence of DAO activity or in the presence of GAC activity selectively without, e.g. substantial influence on DAO or GAC activity; and even more surprising is the selective and effective inhibition by PMSF of esterase activity present in the presence of GAC activity, e.g. because of similar function and structure of acylases and esterases.

In one aspect the present invention provides a process for decreasing, e.g. substantially removing esterase activity present in the presence of D-amino acid oxidase activity or in the presence of glutarylacylase activity in a mixture having esterase activity and D-amino acid oxidase activity and/or glutarylacylase activity, e.g. present in the form of microorganism cells or in the form of a cell-free extract thereof, e.g. in the form of a cell-free extract thereof, comprising treating a mixture having esterase activity and D-amino acid oxidase activity and/or glutarylacylase activity with phenyimethyisulphonyl fluoride, e.g. wherein D-amino acid oxidase activity or glutarylacylase activity remains, e.g. substantially the same after treatment with phenyimethyisulphonyl fluoride as before said treatment. Typically D-amino acid oxidase activity remains more than 91% of the original value and in the case of glutarylacylase activity even more than 97% of the original value.

A process of the present invention may e.g. be carried out as follows: Known and e.g. commercially available microorganisms producing DAO activity include e.g. Trigonopsis, Aspergillus, Penicillium, preferably *Trigonopsis variabilis* microorganisms. Known and e.g. commercially available microorganisms producing GAC activity include e.g Pseudomonas, Achromobacter, *Bacillus cereus* or e.g. transformants, e.g. *E. coli* transformants, e.g. transformed according to e.g. a conventional method. A mixture having DAO activity or GAC activity and esterase activity may e.g. be obtained commercially or e.g. according to a conventional method, and may be e.g. in the form of a cell-free extract, e.g. in immobilised form, or in the form of microorganism cells, such as in the form of e.g. partly purified or impurified cells, and/or permeabilised or non-permeabilised cells, and/or partly destroyed or intact cells, and/or immobilised or non-immobilised cells; such as obtainable from a fermentation broth, e.g. according to a conventional method, preferably in the form of a cell-free extract, e.g. immobilized. E.g. microorganism cells may be isolated, e.g. harvested from a fermentation broth and used as such, e.g. in moist form, e.g. after centrifugation of the fermentation broth, or the cells may be further treated before or after isolation from the fermentation broth, e.g. according to a conventional method, such as homogenising cells to obtain, e.g. partly, destroyed cells, and/or permeabilising cells or fragments thereof to obtain permeabilised cells or cell fragments and/or purifying cells or cell fragments to obtain e.g. partly purified cells and/or cell fragments and/or cell-free (e.g. by cell flocculation) extracts, and/or immobilising cells or cell-free extracts to obtain immobilised cells and/or immobilised cell fragments and/or immobilised cell-free extracts. E.g. immobilisation may be carried out according to a conventional method; e.g. in the presence of acrylic (immobilisation) beads, such as Eupergite® or in the presence of an ion exchange resin, e.g. such as Relite Dianion® according to a method described in the examples below; or e.g. according to another aspect of the present invention which is described below.

The microorganism cells may be used in the form of an, e.g. buffered, aqueous cell suspension, obtainable e.g. by re-suspension of cells in water or in a buffer solution after isolation from a fermentation broth, or in case of a cell-free extract an aqueous solution of the cell-free extract may be used. The pH of a suspension or solution may be, e.g. approximately neutral, e.g. a pH of 6.5 to 8.5, such as 7.0 or around 7.0 may be appropriate.

In a preferred embodiment of the present invention an esterase and DAO activity having mixture may be e.g. substantially, free of e.g. native catalase activity, e.g. obtainable by treatment of an aqueous cell mixture having DAO, esterase and catalase activity in basic medium, e.g. in the presence of a caustic soda solution, e.g. at pH 9 to 11.5, such as 10 to 11.

An esterase activity and DAO activity having mixture or an esterase activity and GAC activity having mixture, may be treated, e.g. incubated at an appropriate temperature, e.g. at room temperature for an appropriate time, e.g. for several hours, such as for 1 to 5, e.g. 2.5 to 4 hours or longer with PMSF, e.g. by addition of a PMSF solution, e.g. of an appropriate concentration range, e.g. of 0.5% to 25%, such as 1% to 10% PMSF in an appropriate solvent, e.g. in alcohol, such as $(C_{1-4})$alkanol, e.g. ethanol. Per 100 liters of a cell suspension an amount of e.g. 1000 ml of PMSF solution, e.g. in a concentration range as indicated above, may be sufficient to remove practically completely and irreversibly undesired esterase activity, e.g. without, e.g. substantially decreasing the DAO or GAC activity present in the starting mixture. Removal of esterase activity may be determined by determination of deacetylation products obtained in G1-7-ACA or 7-ACA reaction from Ceph C using a PMSF-treated DAO or GAC containing mixture. For comparison the reaction may be carried out using a non-PMSF treated DAO or GAC containing mixture under comparable reaction conditions.

A mixture may be obtained wherein DAO or GAC activity is high, e.g. substantially the same as before PMSF treatment and wherein esterase activity is, e.g. substantially, completely removed. A mixture obtainable according to the present invention is useful, e.g. in the production of 7-ACA from e.g. Ceph C. Yields and purity of 7-ACA obtained may be improved if PMSF treated DAO and/or GAC activity is used in comparison with the use of non-PMSF treated DAO and/or GAC activity under comparable reaction conditions. Thus, e.g. the removal of esterase activity according to the present invention, results in less, e.g. substantially no, 3-deacetylation by-products which are due to esterase activity during DAO and or GAC reaction. The undesired amount of 3-deacerylation by-products in G1-7-ACA or 7-ACA obtained by a process according to the present invention may be, e.g. substantially (typically within 1% in a process giving 3% starting activity whereas when PMSF is not used it may increase to 6%), the same as in Ceph C used as starting material.

In another aspect the present invention provides a process for the production of glutaryl-7-aminocephaiosporanic acid comprising the steps
i) treating a mixture having esterase activity and D-amino acid oxidase activity with phenyimethyisulphonyl fluoride, e.g. to obtain a mixture which is substantially free of esterase activity, and e.g. having substantially the same D-amino acid oxidase activity as before PMSF treatment,
ii) reacting cephalosporin C with a mixture obtained in step i) to obtain glutaryl-7-aminocephalosporanic acid, and isolating giutaryl-7-aminocephalosporanic acid, if desired.

In another aspect the present invention provides a process for the production of 7-aminocephalosporanic acid comprising the steps
i) treating a mixture having esterase activity and D-amino acid oxidase activity with phenyimethyisulphonyl fluoride, e.g. to obtain a mixture which is substantially free of esterase activity, and e.g. having substantially the same D-amino acid oxidase activity as before PMSF treatment,
ii) reacting cephalosporin C with a mixture obtained in step i) to obtain glutaryl-7-amino-cephalosporanic acid,
iii) converting glutaryl-7-aminocephalosporanic acid into 7-aminocephalosporanic acid, and isolating 7-aminocephalosporanic acid obtained, if desired.

Conversion of glutaryl-7-aminocephalosporanic acid into 7-aminocephalosporanic acid may be carried out according to a conventional method, e.g. chemically or enzymatically, or e.g. according to another aspect of the present invention, e.g. as described herein.

In another aspect the present invention provides a process for the production of 7-amino cephalosporanic acid comprising the steps
i) treating a mixture having esterase activity and D-armino acid oxidase activity with phenyimethyisulphonyl fluoride, e.g. to obtain a mixture which is substantially free of esterase activity, and e.g. having substantially the same D-amino acid oxidase activity as before PMSF treatment,
ii) reacting cephalosporin C with a mixture obtained in step i) to obtain giutaryl-7-armino cephalosporanic acid,
iii) treating a mixture having esterase activity and glutarylacylase activity with phenyimethyisulphonyl fluoride, e.g. to obtain a mixture which is substantially free of esterase activity, and e.g. having substantially the same glutarylacylase activity as before PMSF treatment,
iv) reacting glutaryl-7-aminocephalosporanic acid obtained in step ii) with a mixture obtained in step iii) to obtain 7-aminocephalosporanic acid; and isolating 7-aminocephalosporanic acid obtained in step ii), if desired.

A process of the present invention to obtain 7-ACA from Ceph C may e.g. be carried our as follows: The starting material Ceph C may be e.g. in the form of an aqueous suspension or solution of Ceph C in free-form or in salt form; e.g. Ceph C may be e.g. in the form of a Ceph C containing fermentation broth, e.g. wherein cells and solid have been removed, e.g. according to a conventional method, or in the form of a salt of Ceph C, e.g. in the form of a sodium salt. The suspension or solution of Ceph C may be treated with a mixture having DAO activity which is pre-treated with PMSF according to the present invention, e.g. in a form as described above, e.g. an aqueous microorganism cell suspension or a cell-free extract may be added to an aqueous suspension or solution of Ceph C (or vice versa); under introduction of oxygen into the suspension or solution, e.g. in the form of oxygen gas or in the form of air, or mixtures thereof, e.g. if desired under pressure.

The reaction may be carried out at appropriate pH, e.g. at around neutral pH, e.g. at a pH of between 6.5 to 8.0, such as 7.0 to 7.5, at appropriate temperatures such as 10° C. to 30° C., e.g. at room temperature. The amount of DAO activity, e.g. the amount of a cell suspension or of a cell-free extract having DAO activity in respect with the amount of Ceph C is depending on the DAO activity present in the cell suspension used and on the amount of Ceph C to be reacted and is not critical; an amount e.g. necessary for a short reaction time may be easily determined e.g. by determination of the amount of G1-7-ACA formed in the mixture during, e.g. regular time intervals by a conventional method, e.g. by HPLC determination.

G1-7-ACA obtained may be isolated and purified, e.g. by a conventional method or may be used as such for further processing, e.g. in the production of 7-ACA.

Oxidase activity may be determined as follows: 0.2 to 5 g of a mixture having DAO activity in the form of permeabilised cells is suspended under stirring in an aqueous 20 mM Ceph C solution at pH 8.0, at 25° C. under introduction of an of oxygen stream into the mixture to oxygen saturation.

The increase of G1-7-ACA and KA-7-ACA is determined by HPLC. The activity of "1 U oxidase" corresponds to the formation of 1 μmol/min G1-7-ACA and KA-7-ACA under the above conditions.

An aqueous solution or suspension of G1-7-ACA, e.g. obtainable or obtained according to the present invention may be brought into contact with a mixture having GAC activity which is pretreated with PMSF according to the present invention, e.g. an aqueous, e.g. buffered cell suspension or a cell-free extract may be added to an aqueous suspension or solution of G1-7-ACA (or vice versa). The reaction may be carried out at appropriate pH, e.g. at slightly basic pH, e.g. including an pH of between 7.5 to 8.5, such as around 8.2, at appropriate temperatures including 10° C. to 30° C., e.g. room temperature. The amount of GAC activity in respect with the amount of G1-7-ACA is depending on the GAC activity present in the cell suspension or in the cell-free extract used and on the amount of G1-7-ACA to be reacted and is not critical; an amount e.g. necessary for a short reaction time may be easily determined e.g. by determination of the amount of 7-ACA formed in the mixture during, e.g. regular time intervals by a conventional method, e.g. by HPLC determination.

GAC activity may be determined as follows: 0.5 g to 2.0 g of a mixture having GAC activity are suspended under stirring in a 2% aqueous G1-7-ACA solution containing 5 mM phosphate and of a pH of 8.0 at 37° C. The pH is kept at 8.0 by addition of an aqueous 100 mM sodium hydroxide solution. The amount of sodium hydroxide used is determined and corresponds to the amount of glutric acid or 7-ACA, respectively formed from G1-7-ACA. The activity of "1 U acylases" corresponds to the formation of 1 μmol/min glutaric acid or 7-ACA, respectively under the above conditions.

7-ACA obtained may be isolated and purified, e.g. by a conventional method, or, if desired may be used as such, e.g. for further processing, e.g. in a 7-ACA reaction, e.g. according to a conventional method.

7-ACA obtained according to the present invention may be of high purity, e.g. 7-ACA obtained may contain a low amount of 3-deacetylation products and may be obtained in high yields; e.g. in yields which are higher than in a process wherein a non pretreated DAO activity and/or a non-pretreated GAC activity is used under comparable reaction conditions.

It is known that e.g. enzyme containing microorganism cells may be immobilised. Immobilised enzyme containing microorganism cells may be useful e.g. because of the possibility of easy recovering and re-use. Known processes for the production of immobilized microorganism cells may have disadvantages, e.g. immobilised cells having poor enzyme stability and/or low specific enzyme activity may be obtained, and/or the immobilisation process may be complicated. Surprisingly a simple immobilisation process for microorganism cells having an enzyme activity, such as DAO or GAC activity, was now found wherein immobilised cells may be obtained in the form of solid spherical particles which may contain stable and highly specific enzyme activity.

In another aspect the present invention provides a process for the production of spherical particles, e.g. in solid form, from microorganism cells having an enzyme activity, comprising the steps i) treating microorganism cells with a primary or secondary amine containing polymer, ii) contacting an organic solvent which is able to form a two-phase system with water with a mixture of microorganism cells, e.g. adding a mixture of microorganism cells to a solvent which is able to form a two phase system with water, iii) treating a mixture obtained in step ii) with a bifunctional agent; and isolating the spherical particles obtained;

e.g. further comprising
pre-treating the microorganism cells with a bifunctional reagent before carrying out steps i) or ii); and/or
adding a water-miscible solvent to a mixture obtained in step iii) before isolation of the spherical particles. and/or
adding a solid to a mixture obtained in step i) or to the microorganism cells before carrying out step i).

The process of the present invention is useful for immobilising microorganism cells having an enzyme activity which are commonly designated as biocatalysts. Microorganisms which may be used according to the present invention include all types of microorganisms, such as bacterias, yeasts, funghi and actinomycetes, e.g. Trigonopsts, such as *Trigonopsis variabilis*, Agrobacterium, such as *Agrobacterium radiobacter*, Rhodotoruia, such as *Rhodotorula glutinis*, Pleurotus, such as *Pleurotus ostreatus*, Aspergillus, Penicillium, Pseudomonas, Achromobacter, Bacillus, such as *Bacillus cereus*, Schizosaccbaromyces, such as *Schizosaccharomyces pombe*; or e.g. transformants such as e.g. *Eschericbia coli* transformants having an enzyme activity. Enzyme activity includes all types of enzyme activity, such as hydrolase, isomerase, lyase, decarboxylase, oxireductase activity. Examples of microorganism cells having an enzyme activity includes e.g. Pleurotus, e.g. *Pleurotus ostreatus* cells having e.g. penicillin-V acylase activity, Agrobacterium, e.g. *Agrobacterium radiobacter* cells having e.g. hydantoinase and/or N-decarbamoylase activity, Rhodotorula, e.g. *Rhodotorula glutinis* cells having e.g. esterase and/or oxidase activity, Trigonopsis, e.g. *Trigonopsis variabilis* having e.g. DAO activity, Schizosaccharomyces, such as *Schizosaccharomyces pombe* having e.g. GAC activity; and cells of transformants such as *Eschericbia coli* having e.g. GAC and/or esterase activity.

The process of the present invention may be e.g. of particular interest in the production of immobilised microorganism cells which are useful in 7-ACA or HACA production, e.g. starring from Ceph C, such as cells having DAO activity, e.g. in the presence of esterase (and/or deacetyase) activity, and/or cells having GAC activity, e.g. in the presence of esterase (and/or deacerylase) activity.

The process according to the present invention may be carried out as follows: Microorganism cells having enzyme activity may e.g. be obtained from a fermentation broth, e.g. according to a conventional method. Microorganism cells include cells in any form e.g. in the form of, e.g. partly purified or impurified cells, and/or permeabilised or non-permeabilised cells, and/or, e.g. partly, destroyed or intact cells. E.g. microorganism cells may be isolated, e.g. harvested from a fermentation broth and used as such, e.g. in moist form, e.g. after centrifugation of the fermentation broth, or the cells may be further treated before or after isolation from the fermentation broth, e.g. according to a conventional method, such as homogenising cells to obtain, e.g. partly, destroyed cells and/or permeabilising cells or fragments thereof to obtain permeabilised cells or fragments thereof, and/or purifying cells to obtain e.g. partly purified cells and/or cell fragments.

Undesired enzyme activity in microorganism cells may be removed before immobilisation of the cells, e.g. according to a conventional method. E.g. catalase activity in Trigonopsis, e.g. *Trigonopsis variabilis* cells may e.g. be removed by treatment under a basic pH, e.g. a pH of 9 to 12, e.g. by addition of a caustic soda solution, e.g. in a mixture of microorganism cells alone, or in a mixture of microorganism cells in the presence of a primary and/or secondary amine containing polymer, optionally in the presence of additives, such as β-mercaptoethanol, ethylenediamine-N,N,N',N'-tetraacetic acid (EDTA) for some time, e.g. ca. 15 minutes or longer.

According to the present invention the microorganism cells may be pre-treated with a bifunctional agent. A bifunctional agent as used herein is to be understood as a compound having at least two reactive groups which are able to react with primary and/or secondary amine groups, including e.g. giutraldehyde, dimethyl pimelimidate, epichlorhydrin, N,N'-carbonyldiimidazole, 1,4-butanediol-diglycidylether, maleic acid anhydride, dicyclohexylcarbodiimide, hexamethylenediisocyanate, preferably glutraidehyde. Pre-treatment of the cells may be carried out in the fermentation broth, or after isolation of microorganism cells, preferably in the fermentation broth. E.g. the bifunctional agent may be added to a microorganism cell suspension, e.g. in dissolved form, e.g. glutaraldehyde may be used in aqueous solution, e.g. in 10% to 30% aqueous solution and the mixture obtained after addition may be stirred for some time, e.g. 30 minutes to some hours, such as 30 minutes to 5 hours. The amount of the bifunctional agent in respect with the amount of cells is not critical; e.g. per 100 g of dry cell weight e.g. 0.1 g to 100 g, e.g. 5 g to 50 g of a bifunctional agent may be used conveniently; e.g. if glutaraldehyde is used as a bifunctional agent 0.5 g to 200 g, such as 1 g to 100 g of a 25% aqueous solution may be appropriate. After pre-treatment with a bifunctional agent the cells may be harvested and isolated, e.g. according to a conventional method, such as concentrated by microfiltration and/or centrifugation and stored in a cool place, e.g. in frozen state. For further use frozen cells may be thawed and washed with spring water, and, if desired, concentrated, e.g. according to a conventional method such as microfiltration.

The microorganism cells, e.g. pre-treated as described above, may be used in the form of an, e.g. buffered, aqueous cell suspension e.g. by re-suspenion of cells in water after isolation from a fermentation broth and optional further treatment, e.g. at a pH of 6.0 to 10.0, such as 8.0 or around 8.0. If desired, an additive, e.g. as conventional, such as β-mercaptoethanol, ethylenediamine-N,N,N',N'-tetraacetic acid (EDTA) may be added to the suspension, e.g. in a conventional amount. To the suspension obtained a primary and/or secondary amine containing polymer including e.g. a polyethylene amine and a polyvinyiamine, which is preferably water-soluble, e.g. in aqueous solution, such as polyethylene amine in e.g. 10% to 50% aqueous solution, e.g. having a molecular weight of 600,000 to 1,000,000 is added. Primary and/or secondary amine containing polymers are e.g. commercially available or e.g. may be produced according to a conventional method. The amount of a primary and/or secondary amine containing polymer in respect with the dry cell mass is not critical and includes e.g. an amount of 1 g to 100 g, such as 5 g to 70 g, such as 10 g to 30 g per 100 g of dry microorganism cell weight The cellipolymer mixture is contacted with an organic solvent which is able to form a two-phase system with water, e.g. the cell/polymer mixture is introduced into an organic solvent which is able to form a two-phase system with water. Appropriate organic solvents include e.g. trialkyl phosphates. such as tributyl phosphates, e.g. n-tributyl phosphate. alkanes, e.g. n-hexane, n-heptane, aromatic hydrocarbons, e.g. toluene, natural or synthetic oils, e.g. soya oil, silicone oil, diesel oil, aromatic or aliphatic e.g. $(C_{3-8})$alkyl, such as $(C_{4-6})$alkyl, e.g. mono- or di- carboxylic acid alkyl, e.g. $(C_{1-8})$alkyl, such as $(C_{1-4})$alkyl, including e.g. glutaric, succinic, adipic acid dimethyl- or diethylester, benzoic or phthalic acid ethyl-, butyl-, dibutyl- or diisobutylester and anise alcohol, preferably trialkyl phosphate. The amount of organic solvent may be such that the microorganism cell supension may be dispersed in the organic solvent, e.g. by, e.g. laminar, stirring into the solvent; per g of dry cell weight e.g. 1 ml to 100 ml. such as 3 ml to 50 ml of solvent may conveniently be used.

The mixture containing the cells, the polymer and the organic solvent is stirred for some time, e.g. until a homogeneous supension is obtained and treated with a bifunctional agent, including e.g. glutaraidehyde, epichlorohydrin, N,N'-carbonyidiimidazoie, 1,4-butanediol-digiycidylether, maleic acid anhydride, dicyclohexylcarbodiimide, hexamethylenediisocyanate, preferably giutaraidehyde. If a pre-treatment of the microorganism cells with a bifunctional agent was carried out, the same bifunctional agent may conveniently be used as in the pre-treatment. The amount of the bifunctional agent is not critical and includes an amount of e.g. 0.5 g to 100 g of a bifunctional agent per 100 g of dry cell weight, e.g. in case of using glutaraldehyde as a bifunctional agent e.g. 1 g to 200 g of a 5% aqueous solution may conveniently be used. Upon addition of the bifunctional agent to the mixture containing the cells. the polymer and the organic solvent crosslinking may start and may be terminated e.g. within a few minutes and a suspension of, e.g. solid spherical particles of the microorganism cells in the solvent mixture used may be obtained. If desired, the suspension obtained may be contacted with an organic solvent which is water-miscible and which may be harmless in respect with enzyme activity, e.g. which may be non-damaging in respect with enzyme activity, including e.g. alcohols, ketones, polyethylene glycols, glycerol, preferably glycerol, e.g. the cell suspension obtained may be introduced into the organic solvent or the solvent may be introduced into the cell suspension obtained. The amount of the water-miscible organic solvent is not critical and includes an amount which is sufficient to form a liquid-liquid two phase system in the reaction mixture; e.g. per 100 g of dry cell weight conveniently e.g. 100 g to 5000 g and more, e.g. 500 g to 5000 g of a water-miscible organic solvent may be used. Phase separation, e.g. immediate, may occur upon contact of the solvent with the cell suspension. Spherical cell particles, e.g. solid. formed may be in the lower aqueous phase obtained. The upper phase, e.g. containing mainly the organic solvent which is able to form a two phase system with water may be separated easily and, e.g. substantially completely from the lower phase and may be re-used, e.g. in a further immobilisation process. The spherical cell particles obtained may be in solid form and may be isolated form the organic-miscible-solvent phase, e.g. by a conventional method, e.g. by pouring the suspension through a vessel with perforated bottom, centrifugation, filtration. The isolated spherical particles may be freed from solvent residues, e.g. washed, e.g. with spring water.

Prior to crosslinking, i.e. prior to addition of the bifunctional agent, e.g. prior to addition of a solvent which is able to form a two-phase system with water, a solid, including e.g. aluminium oxide, activated carbon, bentonite may be added to the mixture of cells. The amount of a solid is not critical; conveniently an amount of 5 g to 200 g, such as 50 g to 150 g per 100 g dry cell weight may be used. After suspension in the solvent which is able to form a two phase system with water and crosslinking by addition of the bifunctional agent into such a mixture, spherical cell particles may be obtained which may particularly easy be separated and which may have a favourable narrow size-distribution-range and excellent mechanical stability.

The biocatalysts, e.g. spherical microorganism cell particles, e.g. in solid form, obtained according to the present invention may be stored for later use e.g. in a cool place, e.g. in an appropriate buffer or e.g. in frozen form or lyophilised form.

Spherical particles containing microorganism cells which contain enzyme activity obtainable, e.g. obtained, according to the present invention are novel.

In another aspect the present invention provides spherical particles containing microorganism cells, e.g. in solid form, which contain enzyme activity obtainable, e.g. obtained, from a process comprising the steps
  i) treating microorganism cells having enzyme activity with a primary or secondary amine containing polymer,
  ii) contacting an organic solvent which is able to form a two-phase system with water with a mixture of microorganism cells, e.g. after carrying out step i), e.g. by addition of a mixture of microorganism cells to a solvent which is able to to form a two-phase system with water,
  iii) treating a mixture obtained in step ii) with a bifunctional agent; and isolating the spherical particles obtained;
    e.g. further comprising
      pre-treating the microorganism cells with a bifunctional reagent before carrying out steps i) or ii); and/or
      adding a water-miscible solvent to a mixture obtained in step iii) before isolation of the spherical particles; and/or
      adding a solid to a mixture obtained in step i) or to microorganism cells before carrying out step i).

Spherical particles, e.g. solid, having an enzyme activity obtained according to a process of the present invention may be useful in enzymatic reactions, e.g. spherical particles, e.g. solid, having DAO activity, e.g. (pre-)treated with PMSF and spherical particles, e.g. solid having GAC activity, e.g. (pre-)treated with PMSF may be useful in the production of 7-ACA and/or G1-7-ACA and/or HACA.

In another aspect the present invention provides a process for the production of glutaryl-7-aminocephalosporanic acid comprising the steps
  i) treating microorganism cells having D-amino acid oxidase activity with a primary or secondary amine containing polymer,
  ii) contacting an organic solvent which is able to form a two-phase system with water with a mixture of microorganism cells, e.g. after carrying out step i), e.g. by addition of a mixture of microorganism cells to a solvent which is able to to form a two-phase system with water,
  iii) treating a mixture obtained in step ii) with a bifunctional agent; and isolating the spherical particles obtained, and if desired, treating a mixture having esterase activity in the presence of D-amino acid oxidase activity with phenyimethyisulphonyl fluoride, e.g. before step iii), e.g. before step i); or treating spherical particles obtained in step iii) having esterase activity in the presence of D-amino acid oxidase activity with phenyimethyisulphonyl fluoride,
  iv) reacting cephalosporin C with spherical particles obtained in step iii) to obtain glutaryl-7-aminocephalosporanic acid, and isolating glutaryl-7-aminocephalosporanic acid, if desired; e.g. and further converting glutaryl-7-aminocephalosporanic acid obtained in step iv) into 7-aminocephalosporanic acid.

In another aspect the present invention provides a process for the production of giutaryl-7-aminocephalosporanic acid which comprises reacting cephalosporin C with spherical particles obtainable by step iii) to obtain glutaryl-7-aminocephalosporanic acid, and isolating glutaryl-7-aminocephalosporanic acid, if desired.

Conversion of glutaryl-7-aminocephalosporanic acid obtained in step iv) into 7-aminocephalosporanic acid may e.g. be carried out according to a conventional method, e.g. chemically or enzymatically, or according to another aspect of the present invention, e.g. using spherical particles having GAC activity obtainable or obtained as described above according to the present invention. If according to the present invention spherical particles are used having DAO enzyme activity in the presence of deacerylase activity; and/or having GAC activity in the presence of deacerylase activity, HACA may be obtained in a reaction with Ceph C or G1-7-ACA.

In another aspect the present invention provides the use of a process for the production of spherical particles according to the present invention or the use of spherical particles produced according to the present invention in the production of 7-amino-3-hydroxymethyl-3-cephem-4-carboxylic acid from cephalosporin C or from glutaryl-7-aminocephalosporanic acid.

7-ACA or HACA produced according to the present invention may be useful as an intermediate in the production of a cephalosporin, e.g. a cephalosporin antibiotic or another intermediate in the production thereof, e.g. by
  acylating the amine group in position 7 of the ring system
  further reacting the acetoxymethyl group in position 3 of the ring system
  esterification of the carboxy group in position 4 of the ring system
  salt and/or solvent formation,
e.g. as described above.

In another aspect the present invention provides a process for the production of 7-aminocephalosporanic acid comprising the steps i) treating microorganism cells having giutarviacyiase activity with a primary or secondary amine containing polymer,
ii) contacting an organic solvent which is able to form a two-phase system with water with a mixture of microorganism cells,
iii) treating a mixture obtained in step ii) with a bifunctional agent; and isolating the spherical particles obtained,
iv) if desired, treating a mixture having esterase activity in the presence of glutarylacylase activity with phenyimethyisulphonyl fluoride, e.g. before step iii), e.g. before step i) if desired; or treating spherical particles obtained in step iii) having esterase activity in the presence of glutarylacylase acylase with phenyimethyisulphonyl fluoride, if desired,
v) reacting glutaryl-7-aminocephaiosporanic acid with spherical particles obtained in step iii) or obtained in step iv) to obtain 7-aminocephalosporanic acid; and isolating 7-aminocephaiosporanic acid obtained, if desired.

In another aspect the present invention provides a process for the production of a cephalosporin, e.g. a cephalosporin antibiotic or an intermediate in its production, wherein 7-aminocephalosporanic acid or 7-amino-3-hydroxymethyl-3-cephem-4-carboxylic acid, e.g. 7-aminocephalosporanic acid, produced according to the present invention is used as an intermediate.

"Substantially" as used herein means e.g. greater than 95%, e.g. 96%, 97% of the original value or less than 5%, e.g. 4%, 3% of the original value as appropriate.

In the following examples all temperatures are given in degrees Celsius. The following abbreviations are used:

7-ACA: 7-aminocephalosporanic acid
Ceph C: Cephalosporin C
DAO D-amino acid oxidase
GAC: glutarylacylase
GDA: glutaraldehyde
GA-7-ACA: Glutaryl-7-aminocephalosporanic acid
KA-7-ACA: α-ketoadipoyl-7-aminocephalosporanic acid
PEI Polyethylene imine
PMSF: Phenyimethyisulphonyl fluoride
TBP: n-Tributyl phosphate The activity of "1 U oxidase" corresponds to the formation of 1 $\mu$mol/min G1-7-ACA and KA-7-ACA in an oxygen saturated 20 mM aqueous Ceph C solution at pH 8 and 25° C. The activity of "1 U acylase" corresponds to the formation of 1 $\mu$mol/min glutaric acid or 7-ACA in a 2% aqueous G1-7-ACA solution at pH 8 and 37° C.

EXAMPLE 1

General Procedure to Obtain a Mixture Having DAO Activity Which is Substantially free of Esterase Activity From an aqueous fermentation broth having esterase activity and DAO activity in water, a cell pellet is obtained from harvested cells according to a conventional method (see e.g. Kubicek-Pranz, E. M. et al., Can. J. Microbiol. 1985, 31, pp 624–628), 10 g of the cell pellet obtained are re-suspended in 50 ml of water and treated for ca. 90 minutes at a pH of ca. 11 with a caustic soda solution at room temperature to remove catalase activity. The pH of the mixture is adjusted to ca. 7 by addition of phosphoric acid.

To the mixture obtained 500 $\mu$l of an ethanolic solution containing 10 mg of PMSF/ml ethanol are added and the mixture obtained is incubated at room temperature for ca. 3 hours. The cell suspension obtained may be used as such in a reaction which requires DAO activity.

DAO activity of cell pellet: 530 U oxidase;
DAO activity after caustic soda treatment: 490 U oxidase;
DAO activity after PMSF treatment: 450 U oxidase (=92% of activity before PMSF treatment).

EXAMPLE 2

A PMSF-treated cell suspension having DAO activity obtained as described example 1 is added to a solution of 10 g Ceph C in 1000 ml of water and the pH of the solution obtained is adjusted to 7.5.

The mixture obtained is stirred for ca. 180 minutes at room temperature under introduction of oxygen into the mixture.

Yield of G1-7-ACA: 91%. Sum of 3-deacerylation products in the starting Ceph C solution: 3% relative to Ceph C; Sum of 3-deacetylation products in reaction solution obtained: 3% relative to starting Ceph C.

Example 2 is repeated but using a DAO activity without PMSF treatment

Yield of G1-7-ACA: 88%. Sum of 3-deacetylarion products in the starring Ceph C solution: 3% relative to Ceph C; Sum of 3-deacetylation products in reaction solution obtained: 6% relative to starting Ceph C.

EXAMPLE 3

A cell suspension obtained as described in example 1 is homogenised before PMSF treatment (DAO activity in nomogenised cells: 385 U oxidase) and the homogenised cells obtained are treated with PMSF as described in example 1 (DAO activity in homogenised and PMSF treated cells: 372 U oxidase corresponding to 96% of activity before PMSF treatment). The cell suspension obtained is reacted with Ceph C as described in example 1.

Yield of G1-7-ACA: 93%; Sum of 3-deacerylation products in starting Ceph C solution: 3% relative to Ceph C; Sum of 3-deacerylation products in reaction solution obtained: 3% relative to starting Ceph C.

Example 3 is repeated but using a DAO activity without PMSF treatment.

Yield of G1-7-ACA: 89%. Sum of 3-deacetyiation products in starting Ceph C solution: 3% relative to Ceph C; Sum of 3-deacetylation products in reaction solution obtained: 7% relative to starting Ceph C.

EXAMPLE 4

10 g of a cell peliet obtained as described in example 1 before caustic soda treatment are suspended in 50 ml of water, 2 g of polyethylene imine imolecular weight 600,000–1,000,000) are added to the supension obtained and the mixture obtained is incubated for 90 minutes at pH 11 (adjusted by caustic soda solution addition) at room temperature. The pH of a mixture obtained is adjusted to 8.5 by addition of phosphoric acid, and the suspension obtained is stirred with 50 ml of toluene. An emulsion of fine droplet-like cell particles in solvent is obtained to which 8 ml of 25% GDA solution are added. The fine dropiet-like cell particles solidify to form solid spherical particles. The solid spherical particles are isolated and washed with spring water. DAO activity in spherical particles: 290 U oxidase The solid spherical particles obtained are suspended in 50 ml of 20 mM phosphate buffer pH 7.0, mixed with 500 µl of PMSF solution analogously as described in example 1 and the mixture obtained is incubated for 180 minutes. DAO activity in PMSF treated solid spherical particles: 305 U oxidase.

The solid PMSF treated spherical particles obtained are used in a Ceph C reaction analogously as described in example 2.

Yield of G1-7-ACA: 92%; Sum of 3-deacetylation products in starting Ceph C solution: 3% relative to Ceph C; Sum of 3-deacervlarion products in reaction solution obtained: 3% relative to starting Ceph C.

Example 4 is repeated but using solid spherical particles without PMSF treatment.

Yield of G1-7-ACA: 89%. Sum of 3-deacerylation products in starting Ceph C solution: 3% relative to Ceph C; Sum of 3-deacerylation products in reaction solution obtained: 7% relative to starting Ceph C.

EXAMPLE 5

10 g of a moist cell pellet of the recombinant *E. coli* strain, e.g. CCM 4229 (GAC activity: 720 U acylase) isolated from the fermentation broth are washed and re-suspended in 50 ml of 50 mM phosphate buffer pH 7.0. To the suspension obtained 0.5 ml of an ethanolic solution containing 10 mg PMSF/ml, are added and the mixture obtained is stirred for ca. 3 hours at room temperature. GAC activity: 708 U acylase (98% of activity before PMSF treatment).

10 g of G1-7-ACA are dissolved in 1000 ml of water and the pH is adjusted to 8.2. The PMSF-treated *E. coli* suspension obtained as described above is added and the mixture obtained is stirred for ca. 180 minutes at 12° whilst maintaining the pH at ca. 8.0–8.2.

Yield of 7-ACA: 93%; Sum of 3-deacetylation products in starting G1-7-ACA solution: 3% relative to G1-7-ACA; Sum of 3-deacervlarion products in reaction solution obtained: 3% relative to starting G1-7-ACA.

Example 5 is repeated but using GAC activity without PMSF treatment.

Yield of G1-7-ACA: 90%. Sum of 3-deacetylation products in starting G1-7-ACA solution: 3% relative to G1-7-ACA; Sum of 3-deacetylarion products in reaction solution obtained: 7% relative to starting G1-7-ACA.

EXAMPLE 6

10 g of a moist washed cell pellet of the recombinant *E. coli* strain, e.g. CCM 4229 (GAC activity: 720 U acylase) are suspended in 50 ml of 50 mM phosphate buffer pH 7.0 and homogenised under a pressure of 700 bar. The homogenised cells (GAC activity: 752 U acylase) are mixed with ethanolic PMSF solution as described in example 5. GAC activity in PMSF treated cells: 768 U acylase.

The suspension obtained is added to a G1-7-ACA solution and the reaction is carried out as described in example 5.

Yield of 7-ACA: 89%; Sum of 3-deacerylation products in starring G1-7-ACA solution: 3% relative to G1-7-ACA; Sum of 3-deacetyiation products in reaction solution obtained: 3% relative to starting G1-7-ACA.

Example 6 is repeated but using GAC activity without PMSF treatment

Yield of G1-7-ACA: 83%. Sum of 3-deacervlarion products in starting G1-7-ACA solution: 3% relative to G1-7-ACA; Sum of 3-deacerylation products in reaction solution obtained: 6% relative to starting G1-7-ACA.

EXAMPLE 7

Homogenised cells from 10 g of a moist washed cell pellet of recombinant *E. coli* strain, e.g. CCM 4229 cells (GAC activity 7350 U acylase) are suspended in 50 ml of 50 mM phosphate buffer pH 7.0 and mixed with a flocculation agent (1 ml of Sedifloc® CL 900-18/40). The pH of the mixture obtained is adjusted to 5.2 by addition of acetic acid and the mixture obtained is incubated for ca 1 hour at ca. 40° under stirring and stirred ca. for a further hour at 10°. The mixture obtained is cleared by centrifugation and the GAC-containing cell-free supernatant (GAC activity: 6150 U acylase) is adjusted to pH 7.5, mixed with PMSF solution and incubated analogously as described in example 5. GAC activity of the cell-free extract obtained after PMSF treatment: 6220 U acykase.

The mixture obtained is mixed with 10 g of acrylic (immobilisation) beads (Eupergit® C), treated with 50 ml of an aqueous 1 mol sodium sulphate solution and incubated for 64 hours at room temperature under shaking. The enzyme-charged carrier material obtained is separated from the immobilisation solution and used as catalyst in a reaction with a G1-7-ACA solution analogously as described in example 5.

Yield of 7-ACA: 90%; Sum of 3-deacetylation products in starting G1-7-ACA solution: 3% relative to G1-7-ACA; Sum of 3-deacerylation products in reaction solution obtained: 3% relative to starting G1-7-ACA.

Example 7 is repeated but using immobilised GAC activity without PMSF treatment.

Yield of G1-7-ACA: 83%. Sum of 3-deacerylation products in starting G1-7-ACA solution: 3% relative to G1-7-ACA; Sum of 3-deacetylation products in reaction solution obtained: 6% relative to starting G1-7-ACA.

EXAMPLE 8

GAC activity is immobilised analogously as described in example 7, but PMSF treatment is not carried out after immobilisation but during immobilisation by addition of 1 ml of PMSF solution analogously as described in example 5 to a mixture containing the GAC-containing cell-free supernatant, Eupergit and sodium sulphate.

The enzyme-charged PMSF treated carrier material obtained is separated from the immobilisation solution and used as a catalyst in a reaction with a G1-7-ACA solution analogously as described in example 5.

Yield of 7-ACA and deacerylation products are substantially as described in example 7.

EXAMPLE 9

GAC-containing supernatant is produced analogously as described in example 7, but without PMSF treatment (GAC activity: 5830 U acylase). The solution obtained is mixed with 40 g of an ion exchange resin (Relite® Diaion-HPA25L), the mixture obtained is adjusted to pH 7.5 and incubated for ca. 300 minutes at room temperature under shaking. The ion exchange resin obtained is isolated and washed (GAC activity: 1865 U acylase).

The exchange resin obtained is suspended in 200 ml of 50 mM phosphate buffer, 2 ml of the PMSF solution as used in example 5 are added and the mixture obtained is incubated for ca. 180 minutes under stirring. GAC activity in the PMSF treated ion exchange resin: 1810 U acylase corresponding to 97% of the activity in the catalyst before PMSF treatment The enzyme-charged PMSF treated ion exchange resin obtained is used as a catalyst in a reaction with a G1-7-ACA solution analogously as described in example 5. Sum of 3-deacerylation products in starting G1-7-ACA solution: 3% relative to G1-7-ACA Sum of 3-deacerylation products in reaction solution obtained: 3% relative to starting G1-7-ACA

EXAMPLE 10 a. Pre-treatment

Cells of *Trigonopsis variabilis*, e.g. ATCC 58536 (535 g moist weight, DAO activity: 25,970 U oxidase) are pre-treated in 2.7 kg of a fermentation broth by stirring 21 g of an aqueous 25% GDA solution into the fermentation broth during ca. 1 hour at room temperature and at pH 7.5. The cells are harvested from the cell suspension obtained by centrifugation and stored in a frozen state. The frozen cell mass is thawed, washed with spring water by means of micro-filtration and concentrated to a volume of ca. 735 ml. DAO activity in the concentrated cell mass: 26,350 U.

b. Polymer Treatment 735 ml of the cell mass obtained as described in step a. (100 g cell dry weight) are suspended with :mercaptoethanol (5 mM), EDTA (2 mM) and 40 g of an aqueous 50% PEI solution, molecular weight 600,000–1,000,000 in water (ca. 800 ml total volume) and stirred slowly for ca. 90 minutes at pH 11 which is adjusted by addition of a caustic soda solution at room temperature. The pH of the mixture obtained is adjusted to pH 9 by addition of phosphoric acid. DAO activity: 24,360 U (94% of pre-treated DAO activity obtained as described in example 10 a.

c. Crosslinking

To 3000 ml of TBP in a stirring vessel the cell/polymer mixture obtained in step b. is added at room temperature under stirring. A homogeneous dispersion of the cellipolymer droplets in TBP is obtained within ca. 30 minutes to which 40 g of an aqueous 25% GDA solution are added. Crosslinking starts immediately and is terminated after some minutes and the cells are obtained in the form of solid spherical particles. 2000 g of glycerol are added to the mixture obtained at 15° to 20° and phase separation between the TBP phase and the aqueous phase is achieved. The lower phase containing mainly glycerol and solid spherical cell particles is separated from the upper phase containing mainly TBP. The upper phase obtain ed (2900 th) may be re-used e.g. in another crosslinking bat ch. The solid spherical particles arc isolated from the lower phase after ca. 90 minutes and washed with spring water in order to remove TBP and glycerol residues. 580 g of moist solid spherical particles having oxidase activity are obtained, corresponding to 121 g of dry weight Specific DAO activity in the solid spherical particles is 32 U/g moist weight (153 U/g dry weight), i.e. total DAO activity is 18,560 U (71% of the pre-treated DAO activity obtained as described in example 10 a.

EXAMPLE 11

580 g of the solid spherical particles (moist weight) obtained in example 10 c. are suspended in 2000 ml of spring water and stirred at room temperature. 20 mg of PMSF are dissolved in 20 ml of absolute ethanol and the solution obtained i s added to the oxidase suspension within ca. 2 minutes. The mixture is incubated for ca. 3 hours, the solid spherical particles obtained are isolated and washed with aqueous ethanol (1000 ml, 10%) and with spring water. 563 g of solid spherical particles (moist weight; corresponding to 138 g of dry weight) are obtained. Specific DAO activity in the PMSF treated solid spherical particles is 31 U/g moist weight (148 U/g dry weight), i.e. total DAO activity is 17,450 U (67% of the pre-treated DAO activity obtained as described in example 10 a. and 94% of the activity before PMSF treatment). The esterase activity in the spherical particles obtained is substantially removed.

EXAMPLE 12

The pH of a cell/polymer mixture produced as described in examples 10 a. and b. is adjusted to 9.0 by addition of phosphoric acid and 80 g of aluminium oxide are added. Crosslinking is carried out with the mixture obtained as described in example 10 c.

630 g of solid spherical particles (moist weight, corresponding to 193 g of dry weight) are obtained. Specific DAQ activity in the solid spherical particles is 26 U/g moist weight (85 U/g dry weight), i.e. total DAO activity is 16,440 U (63% of the pre-treated DAO activity obtained as described in ex ample 10 a.). A narrow size-distribution-range of the particles of 240–500 μm is obtained.

EXAMPLE 13

Is carried out analogously as described in example 10 but without addition of glycerol. After crosslinking the suspension is stirred for ca. 60 minutes. The solid spherical particles obtained in TBP suspension are isolated by running the suspension obtained through a vessel having a perforated bottom, wherein the perforation holes are smaller than the size of the solid spherical particles obtained. 2680 ml of TBP are obtained. TBP residues are removed from the solid spherical particles obtained by washing with spring water.

610 g of solid spherical particles (moist weight, corresponding to 126 g of dry weight) are obtained. Specific DAO activity in the solid spherical particles is 36 U/g moist weight (174 U/g dry weight), i.e. total activity is 21,960 U (85% of the pre-treated DAO activity obtained as described in example 10 a.

EXAMPLE 14

PMSF treated solid spherical particles obtained analogously as described in examples 10 and 11 (81 g moist weight, DAO activity: 2,500 U) are mixed with 1 litre of a 75 mM aqueous Ceph C solution of pH 7.2. Air under 5 bar pressure is introduced into the mixture obtained for ca. 80 minutes. The solution is separated off from the solid spherical particles and is analysed by HPLC. 0.6 mM Ceph C, 70.7 mM G1-ACA and 3 mM of KA-7-ACA are determined in the separated solution.

Example 14 is repeated 142 times each time using a fresh Ceph C-solution and each time using the same PMSF treated solid spherical particles described above in example 14.

The solution is separated off from the solid particles in batch 142 after ca. 160 minutes of contact with Ceph C and is analysed by HPLC. 0.5 mM Ceph C, 69.8 mM G1-ACA and 0.4 mM of KA-7-ACA are determined in the separated solution.

After batch 142 the solid spherical particles had been used for 308 hours. 93 g of solid spherical particles (moist weight, corresponding to 24 g of dry weight) are isolated.

Specific DAO activity in the solid spherical particles obtained is 12 U/g moist weight corresponding to 47 U/g dry weight, i.e. total activity is 1,120 U (45% of the original activity).

EXAMPLE 15

Cells of *Schizosaccharomyces pombe*, e.g. ATCC 38399 and e.g. ATCC 38436 (82 g and 90 g moist weight, respectively) having DAO activity are each pre-treated (separately) analogously as described in example 10 a. with 3.3 g of an aqueous 25% GDA solution and harvested and stored in a frozen state. After thawing the mixture is washed with spring water and concentrated to obtain 20.4 g of dry substance in 164 ml from e.g. ATCC 38399 and 24.1 g of dry substance in 180 ml from e.g. ATCC 38436.

7 g of cell dry weight of each of e.g. ATCC 38399 and e.g. ATCC 38436 are treated (separately) with 2.8 g of an aqueous 50% PEI solution as described in example 10 b.

Crosslinking is carried out with both suspensions obtained (separately) analogously as described in example 10 c. in 230 ml TBP under addition of 3.5 g of an aqueous 25% GDA solution and under addition of 400 g of glycerol. The solid spherical particles obtained are washed with spring water over a sieve in order to remove glycerol and TBP residues.

59.5 g moist weight of solid spherical particles having DAO activity (14.0 g dry weight) are obtained from e.g. ATCC 38436 and 55.6 g moist weight of solid spherical particles having DAO activity (16.1 g dry weight) are obtained from e.g. ATCC 38399. The solid spherical particles obtained show similar DAO reaction characteristics and similar stability characteristics as the spherical particles obtained as described in example 10 c.

*Schizosaccharomyces pombe* is suitable for the cloning and expression of various enzymes. Other biocatalysts, e.g. solid spherical particles having other enzyme activity may be obtained in a simple manner analogously as described in the present example.

EXAMPLE 16

Cells of Pleurotus oszretzus (90 g moist weight, 18,970 U penicillin V acylase) are pretreated with 3.3 g of an aqueous 25% GDA solution analogously as described in example 10 a. The cells from the cell suspension obtained are harvested, stored in a frozen state, and after thawing are washed with spring water and concentrated by microfiltration.

18.6 g of cells obtained (dry weight) are treated with 7.4 g of an aqueous 50% PEI solution. Cell crosslinking is carried out analogously as described in example 10 c. in 560 ml TEP under addition of 7.4 g of an aqueous 25% GDA solution and under addition of 370 g of glycerol. The solid spherical particles obtained are washed with spring water through a sieve in order to remove glycerol and TBP residues.

223 g of solid spherical particles containing penicillin V acylase (moist weight corresponding to 29.4 g dry weight) are obtained. Specific penicillin V acylase is 50.4 U/g moist weight, i.e. total penicillin V acylase is 11,240 U (59% the original activity).

1 U penicillin V acylase corresponds to the formation of 1 μmol per minute of 6-aminopenicillanic acid in an aqueous phosphate-buffered K-penicillin-V solution (50 g/l) at pH 7.5 and 28°.

EXAMPLE 17

Cells of *Trigonopsis variabilis*, e.g. ATCC 58536 (54 g moist weight, DAO activity: 2,600 U oxidase) are produced analogously as described in examples 10 a. and 10 b. Crosslinking is effected analogously as described in example 10 c., but a cell/polymer mixture containing *Trigonopsis variabilis cells* (ca. 10 g dry weight) is added under stirring into either 300 ml of glutaric dimethylester or 300 ml of adipic dimethylester (instead of 3000 ml of TBP to 100 g cell dry weight). Crosslinking in each of the mixtures obtained (separately) is carried out under addition of 5 g of an aqueous 25% GDA solution to each of the mixtures and under addition of 400 g of glycerol to each of the mixture at a temperature of 15° to 20° analogously as described in example 10 c.

93.4 g and 86.9 g, respectively of solid spherical particles having DAO activity are obtained (moist weight, corresponding to 20.6 g and 20.2 g of dry weight, respectively).

Specific DAO activity is 14.8 U/g moist weight or 12.5 U/g moist weight, respectively, i.e. total activity is 1382 U (53% of the original activity) or 1086 U (42% of the original activity), respectively.

What is claimed is:

1. A process for the production of spherical particles having an enzyme activity from microorganism cells having the enzyme activity, comprising the steps i) directly adding to the microorganism cells a primary or secondary amine containing polymer, ii) mixing the treated microorganism cells from step i) with an organic solvent to form a two-phase system with water, and iii) adding to the mixture obtained from step ii) a bifunctional agent to yield the spherical particales with the enzyme activity.

2. A spherical particle having an enzyme activity obtained from a process comprising the steps i) directly adding to microorganism cells having the enzyme activity a primary or secondary amine containing polymer, ii) mixing the treated microorganism cells from step i) with an organic solvent to form a two-phase system with water, and iii) adding to the mixture obtained form step ii) a bifunctional agent to yield the spherical particles with the enzyme activity.

3. A spherical particle of claim 2 wherein the enzyme activity is D-amino oxidase activity or glutarylacylase activity.

4. A spherical particle of claim 3 where the process further comprises adding phenylmethylsulphonyl fluoride to the mixture obtained from step ii).

* * * * *

UNITED STATES PATENT AND TRADEMARK OFFICE
CERTIFICATE OF CORRECTION

PATENT NO. : 6,465,227 B1
DATED : October 15, 2002
INVENTOR(S) : Reichert et al.

It is certified that error appears in the above-identified patent and that said Letters Patent is hereby corrected as shown below:

<u>Column 8,</u>
Line 15, should read: -- of 1 g to 100g, such as 5 g to 70 g, such as 10 g to 50 g per --.
Line 42, should read: -- hexamethylenediisocyanate, preferably glutaraldehyde. If a --.
Line 49, should read: -- tional agent e.g. 1 g to 2000 g of a 25% aqueous solution may --.

<u>Column 11,</u>
Line 1, should read: -- i) treating microorganism cells having glutarylacylase --.
Line 41, should read: -- GI-7-ACA: Glutaryl-7-aminocephalosporanic acid --.
Line 45, should read: -- PMSF: Phenylmethylsulphonyl fluoride --.

<u>Column 15,</u>
Line 45, should read: -- mainly TBP. The upper phase obtained (2900 ml) may be --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,465,227 B1
DATED : October 15, 2002
INVENTOR(S) : Reichert et al.

It is certified that error appears in the above-identified patent and that said Letters Patent is hereby corrected as shown below:

Column 8,
Line 15, should read: -- of 1 g to 100g, such as 5 g to 70 g, such as 10 g to 50 g per --.
Line 42, should read: -- hexamethylenediisocyanate, preferably glutaraldehyde. If a --.
Line 49, should read: -- tional agent e.g. 1 g to 200 g of a 25% aqueous solution may --.

Column 11,
Line 1, should read: -- i) treating microorganism cells having glutarylacylase --.
Line 41, should read: -- GI-7-ACA: Glutaryl-7-aminocephalosporanic acid --.
Line 45, should read: -- PMSF: Phenylmethylsulphonyl fluoride --.

Column 15,
Line 45, should read: -- mainly TBP. The upper phase obtained (2900 ml) may be --.

Signed and Sealed this

Thirteenth Day of July, 2004

JON W. DUDAS
*Acting Director of the United States Patent and Trademark Office*